US006673315B2

(12) United States Patent
Sheridan et al.

(10) Patent No.: US 6,673,315 B2
(45) Date of Patent: Jan. 6, 2004

(54) METHOD AND APPARATUS FOR ACCESSING A SITE ON A BIOLOGICAL SUBSTRATE

(75) Inventors: Richard Sheridan, Cary, NC (US); Xue-Feng Wang, Chapel Hill, NC (US)

(73) Assignee: BioMachines, Inc., Morrisville, NC (US)

( * ) Notice: Subject to any disclaimer, the term of this patent is extended or adjusted under 35 U.S.C. 154(b) by 0 days.

(21) Appl. No.: 10/143,138

(22) Filed: May 9, 2002

(65) Prior Publication Data

US 2003/0027342 A1 Feb. 6, 2003

Related U.S. Application Data (60) Provisional application No. 60/302,191, filed on Jun. 29, 2001.

(51) Int. Cl.[7] .............................................. G01N 21/01
(52) U.S. Cl. ........................ 422/50; 422/63; 422/66; 422/67; 422/99; 422/100; 422/102; 422/104; 422/82.05; 436/43; 436/44; 436/46; 436/164; 436/165; 435/287.1; 356/246
(58) Field of Search .................. 422/50, 63, 66–67, 422/100, 99, 102, 104, 82.05, 941–942; 436/43, 44, 46, 164–165; 435/287.1; 356/246

(56) References Cited

U.S. PATENT DOCUMENTS

| | | | | |
|---|---|---|---|---|
| 3,851,972 A | * | 12/1974 | Smith et al. ................ | 356/39 |
| 4,907,158 A | * | 3/1990 | Kettler et al. ............... | 382/128 |
| 5,000,554 A | * | 3/1991 | Gibbs ......................... | 101/485 |
| 5,643,798 A | | 7/1997 | Beavis et al. ................ | 436/94 |
| 5,721,607 A | * | 2/1998 | Ota .............................. | 355/53 |
| 5,840,256 A | * | 11/1998 | Demers et al. ............. | 204/600 |
| 6,215,894 B1 | * | 4/2001 | Zeleny et al. ............... | 382/133 |
| 6,258,326 B1 | * | 7/2001 | Modlin ....................... | 422/100 |
| 6,362,004 B1 | * | 3/2002 | Noblett ....................... | 356/244 |
| 6,372,185 B1 | * | 4/2002 | Shumate et al. ............ | 422/100 |

FOREIGN PATENT DOCUMENTS

| | | |
|---|---|---|
| EP | 0 571 053 A2 | 11/1986 |
| WO | WO 01/35074 A1 | 10/2000 |
| WO | WO 01/35099 A1 | 10/2000 |

* cited by examiner

*Primary Examiner*—Jill Warden
*Assistant Examiner*—Kathryn Bex
(74) *Attorney, Agent, or Firm*—Sheridan Ross P.C.

(57) ABSTRACT

The present invention provides a method and an apparatus for facilitating the creation and study of biological substrates. In particular, the present invention allows the location of materials deposited on a substrate to be identified, and communicated with great precision. This in turn allows additional biological materials to be deposited as probes over target locations. The present invention also allows for small regions of biological materials deposited on a substrate to be identified and repeatedly accessed, even when the biological substrate has been removed from the device originally used to review the region of interest and is then reinserted into the original device. Furthermore, the present invention allows a region of interest to be accurately located even using a machine that is different from the machine originally used to identify the region of interest.

16 Claims, 8 Drawing Sheets

METHOD AND APPARATUS FOR ACCESSING A SITE ON A BIOLOGICAL SUBSTRATE

CROSS REFERENCE TO RELATED APPLICATIONS

Priority is claimed from U.S. Provisional Patent Application Ser. No. 60/302,191, filed Jun. 29, 2001, entitled A DETERMINATION OF THE LOCATION AND ORIENTATION OF AN OBJECT USING FIDUCIAL MARK AND POSITIVE IDENTIFICATION TECHNIQUES IN BIOSCIENCE APPLICATIONS, the disclosure of which is incorporated herein by reference in its entirety.

FIELD OF THE INVENTION

The present invention is directed to a method and apparatus for accessing a site on a biological substrate. In particular, the present invention is directed to the use of multiple levels of fiducial marks to access a specific site on a biological substrate.

BACKGROUND OF THE INVENTION

Biological substrates, including microarrays, biochips, biosensors, multi-well assay plates, cytology slides and microscope slides are used in connection with a variety of applications. For example, such biological substrates are useful in connection with life science, biotechnology, pharmaceutical, chemical, agriscience, and biomedical manufacturing, development and discovery applications, particularly in genomics, proteomics, cellomics (the microscale analysis of temporal and spatial interactions of cellular components with proteins, genes and exogenous biomaterials), diagnostics, and pathology in which microscopy and biological microchip technologies are used. As such technologies become more advanced, it is increasingly important to access or identify specific sites on a biological substrate with great accuracy and repeatability. However, existing systems or devices for providing access to specific sites on a biological substrate do not provide the precision and repeatability that is increasingly required.

In addition, existing devices for use in connection with biological substrates lack a flexible system for identifying particular areas on a biological substrate for later access. Therefore, the task of locating previously accessed sites is difficult. For example, some cell biology applications require the repeated examination of cell and tissue features over time. In particular, there is a need to allow technicians to review and validate the work of other technicians, and there is a need to track changes in the orientation, position, shape, movement and response of a cell attached to a treated substrate over time. However, current systems available for use in these applications are unable to accurately identify and record the location of specific cells and to facilitate the accurate and precise reexamination of specific cells over time. The inability of existing systems to allow specific cells to be reaccessed is particularly apparent where a substrate to which the cells are attached has been removed from and then reinserted into the device, or where a subsequent access operation is conducted using a device that is different from the device initially used to access the cells. The inability of existing devices to identify, record and communicate the accurate location of cells is a major barrier to the automation of such applications. Therefore, conventional systems require a time consuming, manual intervention by a knowledgeable user in order to locate the cell feature of interest during a time sequence study. Accordingly, the process is inefficient, and can be difficult to execute repeatedly. The process is also imprecise, resulting in a subjective process characterized by inherent variability.

Another application for systems capable of precisely positioning biological materials is found in connection with microarrays. Microarrays are sets of densely spaced, miniaturized chemical or biochemical reaction sites (or spots) on a microscope slide or other solid supports. Examples of microarrays include: DNA, protein, cell tissue, antibody, vaccine, and antiviral arrays. The reaction sites are typically arranged in an array or a grid pattern. The sites may be deposited on the substrate by contact printing using pins or capillaries, or non-contact printing using an inkjet, piezoelectric or magnetostrictive actuated microdispenser, micro-electro-mechanical systems (MEMS) microfluidics dispenser, or syringe solenoid liquid handling device. Information regarding the precise location of the grid and the grid nodes (i.e. the reaction sites) on the substrate is required to properly analyze the sites. The deposition of material in a grid or matrix facilitates large scale studies, such as: mapping complex biological pathways and systems; screening large numbers of drug targets and potential drug candidates; and performing genomic scans of biallelic markers for identifying disease and drug effect genes. However, conventional array deposition systems are not able to accurately identify and record the location of arrayed materials and to communicate this information to systems used for post-deposition array processing, readout, and analysis. Therefore, the full potential of microarrays has not yet been realized.

In a biochip or biosensor, one or more miniaturized chemical or biochemical reaction sites (or dots) are arranged in a pattern on a substrate. The precise location of the dots on the substrate are biochemically important, since the dots are deposited on preexisting features (or targets), such as activated surface sites or electrodes. If the dots do not precisely align with the preexisting features, the signal to noise ratio may be reduced, resulting in decreased sensitivity. Furthermore, it is important to produce uniform biochips in order to reduce variability in experimental procedures. However, existing devices are incapable of precisely depositing (or targeting) specific sites on a biochip or biosensor surface. Accordingly, the quality and uniformity of biochips and biosensors could be improved.

Therefore, while devices for accessing biological substrates have been developed, systems that provide access with desired levels of precision and repeatability have not been achieved. In addition, systems that provide for the convenient and accurate association of location information regarding a specific site or sites on a particular biological substrate with that substrate have not been achieved. Therefore, a need exists for a system capable of accessing sites on biological substrates with high levels of precision and repeatability. In addition, a need exists for a system that allows for the convenient and accurate association of information regarding a biological substrate with that substrate.

SUMMARY OF THE INVENTION

In accordance with the present invention, a method and an apparatus for accessing specific sites on a biological substrate with a high degree of precision and repeatability are provided. In addition, the present invention provides a method and an apparatus for associating information regarding a biological substrate with that substrate. The present invention allows predetermined sites to be targeted, and additionally allows previously accessed sites to be re-accessed. Accordingly, the present invention has applicability to both the creation of bioactive devices, including microarrays, biochips, and biosensors, and in re-accessing specific areas of a biological substrate on which a specimen is deposited. The present invention therefore has applicability to producing miniaturized and high precision devices utilizing biological materials, and to improving the accuracy and workload of lab technicians.

In accordance with an embodiment of the present invention, a device for accessing a site on a biological substrate is provided. The device utilizes more than one fiducial level system to orient an access device with respect to the biological substrate. Thus, a first fiducial level system may be utilized to establish a first fiducial level datum point, which may coincide to a biological substrate platform datum point. The first fiducial level system may be used for gross positioning of the biological substrate with respect to an access device (or vice versa). In addition, a second fiducial level system may be utilized to establish a second fiducial level datum point with respect to either the biological substrate platform datum point or the first fiducial level system datum point. The second fiducial level system may be used for fine positioning of the access device with respect to the biological substrate. In accordance with a further embodiment of the present invention, additional fiducial level systems may be provided. In addition, multiple instances of a fiducial level system may be provided. For example, a tray containing a plurality of biological substrates may include a second fiducial level system for each biological substrate.

In accordance with an embodiment of the present invention, the access device may include a readout unit, such as a microscope or scanner, or a material deposition unit. The access device may have a reference point or origin, and the position of that reference point with respect to a biological substrate platform datum point may be monitored. A device in accordance with an embodiment of the present invention may utilize sensors for determining the position of various fiducial level systems relative to the access device reference point using one or more sensors appropriate to the type of fiducial marks incorporated in the fiducial level systems. For instance, printed or inscribed fiducial marks may be apprehended by optical sensors. Accordingly, a device in accordance with the present invention may incorporate machine vision capabilities. According to another embodiment of the present invention, the device may utilize magnetic detectors for use in connection with magnetic fiducial marks or fluorescence detectors for use in connection with fluorescent fiducial marks.

Biological substrates that may be used in connection with the device of the present invention include microarrays, biochips, biosensors, multi-well assay plates, and biological sample or cytology slides, or any biological substrate that requires the accurate and precise locating of features below a few thousand microns in size. For instance, in connection with a microarray, which may provide a large number of wells or reaction sites arrayed over a single substrate, a device in accordance with the present invention may be utilized to accurately place biological materials in or remove biological material from the predefined wells or sites. Accordingly, the present invention allows specific sites to be targeted. The targeting capabilities of a device in accordance with the present invention are also useful in connection with the production of biochips, in which the precise deposition of biological material on one or more electrodes or on chemically treated sites is required. Similarly, the targeting of material in connection with biosensor applications is facilitated by the present invention. In connection with biological samples, such as cytology slides, the present invention allows particular cells on such a slide to be accessed quickly and conveniently, even after the slide has been removed from a device and reinserted, and even using different devices.

In a further aspect of the present invention, identifiers are associated with each substrate. These identifiers, which may include numeric or bar codes, allow information regarding the individual biological substrates to be stored in and retrieved from files identified or indexed by the associated identifier. Accordingly, information related to a particular biological substrate may be conveniently accessed by referencing a file or other subset of data associated with the assigned identifier. The identifier may be applied to a biological substrate prior to or following an access operation. In accordance with an embodiment of the present invention, the identifier is provided in the form of a printed label that can be adhered to the biological substrate. In accordance with still another embodiment of the present invention, the printed label includes, in addition to an identifier, fiducial marks included as part of one or more fiducial level systems.

The present invention additionally provides a method for facilitating the accessing of specific sites on a biological substrate with a high degree of precision and repeatability. In general, the method includes utilizing more than one fiducial level system for establishing datum points used to accurately record a location or to re-access a location on a biological substrate. In accordance with an embodiment of the present invention, a first fiducial level system is provided for coarse location and positioning. The first fiducial level system may be associated with a machine platform, with a biological substrate, or with a tray containing one or more biological substrates. In addition, a second fiducial level system is associated with a tray of biological substrates or with an individual biological substrate, and is used for relatively fine positioning operations. Additional fiducial level systems may also be provided.

During an accessing operation, a targeted location may be identified by reference to a fiducial level system associated with the biological substrate being accessed. For example, a particular site may be targeted by receiving location information entered by a user or retrieved from a file associated with the biological substrate by an identifier. Access operations involving a site on a biological substrate that is not predetermined may be carried out, and the precise location that was accessed recorded by reference to a fiducial level system. That information may be recorded in a file associated with the biological substrate by an identifier assigned to the biological substrate. The coordinates of a location on a biological substrate may be given with reference to a fiducial level system associated with the particular biological substrate. These coordinates may be translated into coordinates referenced to a datum point that is established with respect to a machine platform utilized in connection with accessing operations.

The present invention provides a method for standardizing various standalone devices or components of a multi-functional device with respect to accessing specific sites on a biological substrate with a high degree of precision and repeatability. In general, the method includes utilizing a fiducial level system for establishing datum points used to accurately record a location or to re-access a location on a biological substrate. In accordance with an embodiment of the present invention, fiducial level system information can be shared by any number of standalone devices or components of a multi-functional device for accessing specific sites on a biological substrate at any time over the entire lifetime of the substrate. The fiducial level system information associated with the biological substrate is accessed by the various devices acting upon the substrate by an identifier assigned to the biological substrate.

Additional advantages of the present invention will become readily apparent from the following discussion, particularly when taken together with the accompanying drawings.

DETAILED DESCRIPTION

Figure 1:
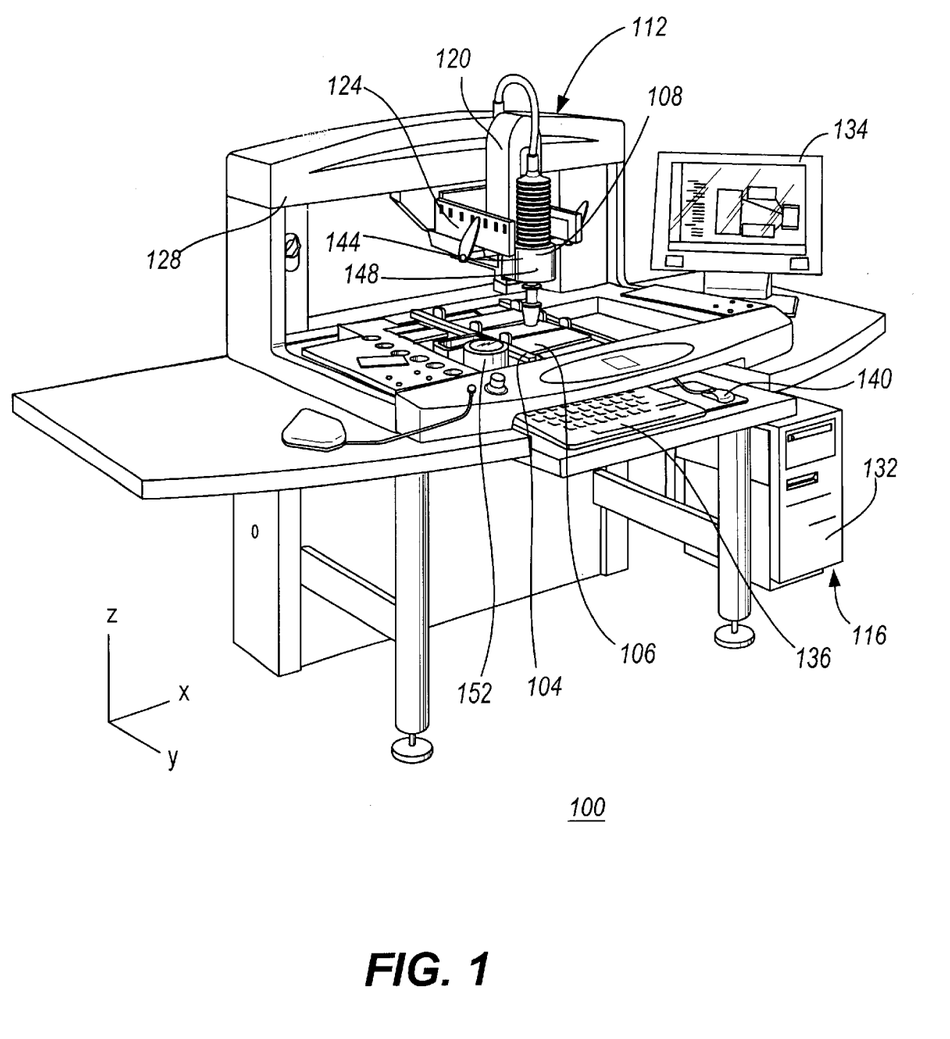
FIG. 1 is a perspective view of a system for accessing sites on a biological substrate in accordance with an embodiment of the present invention.

The present invention is directed to a method and an apparatus for accessing a site on a biological substrate. In FIG. 1, a system 100 for accessing a site on a biological substrate in accordance with an embodiment of the present invention is illustrated. In general, the system 100 includes a biological substrate platform 104, one or more biological substrates 106, an access device 108, an access device carriage 112, and a controller 116. The access device carriage 112 provides for movement of the access device along or about various axes. The access device carriage 112 generally includes a first movable member 120 to permit the access device 108 to move along the Z axis. In addition, the carriage assembly 112 includes a second movable member 124 that permits the access device 108 to move along the Y axis. A third movable member 128 allows movement of the access device 108 along the X axis. The members 120–128, or additional movable members or elements, may also provide for rotational movement of the access device 108 about one or more axes.

The biological substrate 106 may include any substrate containing or adapted to contain one or more biological or bioactive materials. For purposes of the present disclosure, biological or bioactive materials include, in combination or in whole or in part, cell samples, proteins, polypeptides, antibodies, effectors, modulators, carbohydrates, sugars, lipids, new chemical entities, drugs, drug candidates, and nucleic acid molecules. Examples of biological substrates 106 include microarrays, biochips, biosensors, multi-well assay plates, cytological slides and microscope slides.

The access device 108 may be any device capable of interfacing with the biological substrate 106. For example, the access device 108 may comprise an optical sensor such as a microscope or other sensing device capable of deriving information from a biological substrate 106 interconnected to the biological substrate platform 104. Access devices 108 capable of obtaining information from a biological substrate 106 (i.e. readout devices) include optical microscopes and laser scanners. Other access devices 108 capable of obtaining information from a biological substrate 106 include devices capable of detecting fluorescence, absorption, x-rays, radioactive decay, chemiluminescence, bioluminescence, photon emission, pH, electric fields, capacitance, conductance, temperature, heat, morphology and other material attributes. Alternatively or in addition, the access device 108 may comprise a material deposition unit. Examples of material deposition units that may be used in connection with a system 100 in accordance with the present invention include microfluid handling devices that mechanically spot or print targets and probes using various techniques, including photolithography techniques, contact spotting by mechanical pins and capillaries, and non-contact jet, piezoelectric or magnetostrictive actuated microdispenser, MEMS microfluidics dispenser, and syringe solenoid printing. Typical access devices 108 capable of depositing material deliver volumes from about 10 picoliters to about 20 nanoliters to create spots having diameters from about 50 microns to about 1000 microns.

The controller 116 may comprise various components, such as a central processing unit 132, a display 134, and input devices, such as a keyboard 136 and a pointing device 140. Additional inputs may include signals provided by a position sensor 144, an identifier sensor 148, and position sensors associated with the various movable members 120–128 of the carriage 112. Still another input to the controller may include an upward looking sensor 152 capable of, for example, determining the relative location of elements in an access device 108 for depositing an array of material, as will be discussed below. According to an embodiment of the present invention, the central processing unit 132 of the controller 116 comprises a general purpose computer. In accordance with still another embodiment of the present invention, the central processing unit 132 comprises a controller chip adapted for use in connection with the controller 116 of the system 100. In accordance with still another embodiment of the present invention, the system 100, and in particular the controller 116 comprises DSP-based motion and peripheral controllers distributed throughout the system 100 to the locations where actuations are needed or processes need to be monitored. In such an embodiment the system 100 uses a 400 megabit/second IEEE 1394 network to link the hardware elements, including cameras, sensors, motion controllers, and I/O controls to a host PC 116 running a standard operating system such as Microsoft Windows®.

The position sensor 144 may be an optical sensor, and it may have a position that is fixed with respect to one or more degrees of freedom of the access device 108. The identifier sensor 148 may also have a position that is fixed with respect to one or more degrees of freedom of the access device 108. Alternatively, the identifier sensor 148 may be free to move independently of the access device 108. For example, the identifier sensor 148 may be adapted for use by the operator of the system 100 as a handheld device. The upward looking sensor 152 may be an optical sensor. In accordance with an embodiment of the present invention, the upward looking sensor 152 is fixed to the biological substrate platform 104.

Figure 2:
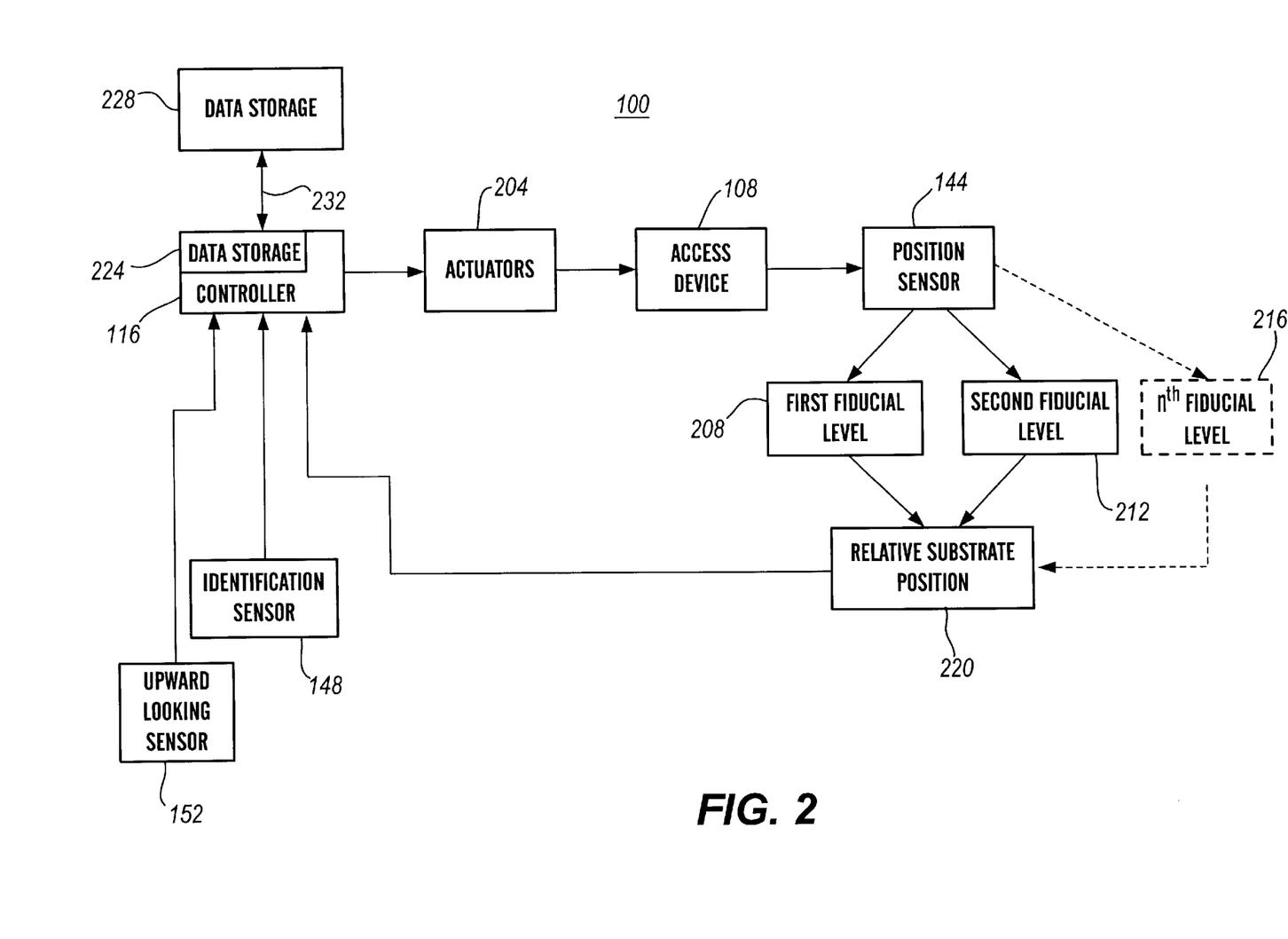
FIG. 2 is functional block diagram of the system of FIG. 1 for accessing sites on a biological substrate.

With reference now to FIG. 2, a system 100 in accordance with an embodiment of the present invention is illustrated in functional block diagram form. In general, the controller 116 functions to provide control signals to the various actuators 204 included as part of the carriage assembly 112. By providing suitable control signals to the actuators 204, the controller 116 can place the access device 108 in a desired position with respect to the biological substrate platform 104. Alternatively, the actuators 204 may move the biological substrate platform 104 with respect to the access device 108 to allow the access device to address a particular site on a biological substrate 106 held by the biological substrate platform 104. In accordance with still another embodiment of the present invention, one or more actuators 204 may move the access device 108 along or about one or more axes, and one or more actuators 204 may move the biological substrate platform 104 along or about one or more axes. The actuators 204 for moving the various carriage members 120–128 may comprise various devices, including linear motors, servo motors and piezoelectric motors.

In general, the position sensor 144 senses the position of the biological substrate 106 interconnected to the biological substrate platform 104 relative to the access device 108. In particular, the position sensor 144 receives position information from at least a first fiducial level system 208 and a second fiducial level system 212. Position information may also be obtained from additional (or nth) fiducial level systems 216.

The first 208, second 212 and nth 216 fiducial level systems may have a hierarchal relationship with one another. In addition, multiple instances of a fiducial level system 208, 212 or 216 may be provided that have a sibling relationship with one another. In a hierarchal relationship, the first fiducial level system 208 may be a global level system provided for relatively coarse positioning of the access device 108 relative to the substrate 106. As a global level system, the first fiducial level system 208 generally applies to a relatively large area or set of features, such as the work area of the biological substrate platform 104, the area of a biological substrate tray 320 (see FIG. 3) capable of receiving biological substrates 106, or the area of a biological substrate 106 in which biological material may be deposited. The second fiducial level system 212 may be provided as a local level system that is used in connection with relatively fine positioning of the access device 108 relative to a biological substrate 106. For example, the second fiducial level system 212 may cover an area or group of features comprising one or more biological substrates 106, or a sub-region of a biological substrate 106, that is itself included within an area encompassed by the first fiducial level system 208. If provided, a third fiducial level system 216 may be utilized in a hierarchal system for even finer positioning. For example, a third fiducial level system 216 may be used in connection with fine positioning of the access device relative to an area or group of features that comprises a sub-region of a biological substrate 106 that is included within an area or group of features encompassed by the second fiducial level system 212. Additional fiducial level systems in a hierarchy may also be provided. Using a hierarchy of fiducial level systems to organize or group features, a desired feature can easily be located by accessing groups of features that are progressively more specific. The present invention allows positioning of the access device 108 with a resolution that has not been achieved by conventional devices. In addition, the present invention allows an access device 108 to access a very small area of a biological substrate 106 repeatably. In accordance with an embodiment of the present invention, the access device 108 may be positioned with respect to a location or feature on a biological substrate 106 with a repeatability of about the square root of a spot or target diameter. For example, such an embodiment for use in connection with a spot having a diameter of 100 $\mu$m could have a repeatability of about 10 $\mu$m. In accordance with another embodiment of the present invention, the access device 108 may be positioned with respect to a location or feature on a biological substrate with a resolution of about ±1 $\mu$m and a repeatability of about ±4 $\mu$m. In a system 100 in which one or more of the provided fiducial level systems include multiple instances that are related as siblings, each fiducial level system 208, 212 or 216 in a sibling relationship relates to an area or group of features that is substantially non-overlapping with the area or group of features of a sibling fiducial level system 208, 212 or 216. For example a first instance of the second fiducial level system 212 may be associated with a first biological substrate 106 including a first group of features, and a second instance of the second fiducial level system 212 may be associated with a second biological substrate 106 including a second group of features. As a further example, in a sibling relationship, a first instance of the second fiducial level system 212 may be related to a first substrate sub-region 604 (see FIGS. 6 and 7) including a first group of features and a second instance of the second fiducial level system 212 may be related to a second substrate sub-region 604 including a second group of features.

It should be noted that a system 100 in accordance with the present invention having fiducial level systems in a sibling relationship with one another also includes at least one other fiducial level system that is in a hierarchal relationship with the set of fiducial level systems 208, 212 or 216 that includes sibling instances. For instance, a system 100 may utilize a first fiducial level system 208 for gross positioning of the access device 108 relative to the biological substrate platform 104. The system may additionally utilize a first instance of a second fiducial level system 212 to position the access device 108 relative to a first biological substrate 106, and may utilize a second instance of the second fiducial level system 212 to position the access device 108 relative to a second biological substrate 106. In this example, it can be appreciated that the instances of the second fiducial level system 212 are both subordinate to the first fiducial level system 208. As still another example, the first and second instances of the second fiducial level system 212 may be subordinate to a first instance of a first fiducial level system 208, and third and fourth instances of the second fiducial level system 212 may be subordinate to a second instance of the first fiducial level system 208.

The position sensor 144 determines the relative position of the access device 108 to points or areas encompassed by a fiducial level system 208, 212 or 216 using techniques known in the art, such as machine vision, or vision sensor-based pattern or object recognition system. In general, fiducial marks 304 (see, e.g., FIG. 3) provided as part of fiducial level systems 208, 212 or 216 are recognized by the position sensor 144, and their position established as a datum point for use in moving the position of the access device 108 relative to the area encompassed by the fiducial level system 208, 212 or 216 to which a particular fiducial mark or marks 304 belongs. The relative position information 220 obtained by the position sensor 144 from the various fiducial level systems 208, 212, and 216 is provided to the controller 116. According to an embodiment of the present invention, the controller 116 tracks the position of the access device 108 relative to a reference or datum point established with respect to the biological substrate platform 104. The relative position may be determined with reference to a fiducial mark 304 on the biological substrate platform 104, or with reference to encoder strips and cooperating encoder sensors provided as part of the carriage assembly 112.

The identification sensor 148 may provide information to the controller 116 related to a particular biological substrate 106 being accessed using the system 100. For example, from an identifier (e.g., identifier 412 illustrated in FIG. 4) sensed by the identification sensor 148 and provided to the controller 116, the controller 116 can access data related to the position of a particular site or sites on that biological substrate 106. In addition, the controller 116 can store information related to a site or sites on a biological substrate 106 accessed by the access device 108. That information can be stored in a file and related to the relevant biological substrate 106 using the identifier sensed by the identification sensor 148.

The upward looking sensor 152 may be an optical sensor, and is generally positioned such that features of an access device 108 may be apprehended. For example, in connection with an access device 108 capable of simultaneously depositing an array of biological material, the positions of the individual deposition elements relative to one another and/or relative to an access device 108 reference point may be determined. The position information may be communicated to the controller 116 for storage in a file to permit more accurate and/or rapid accessing of particular sites within the array during subsequent operations.

The information related to a biological substrate 106 by an identifier can be stored in a data storage device 224 provided as part of the controller 116. The data storage device 224 may be any device suitable for the storage of machine accessible data, including magnetic disk drives, optical disk drives, magnetic tape devices and solid state memory devices. In addition or alternatively, the information related to biological substrates 106 may be stored in one or more data storage devices 228 that are external to the controller 116. The external data storage device or devices 228 may be in communication with the controller 116 via a bus or computer network 232. In accordance with the present invention, an external data storage device 228 may be any device suitable for the storage of machine accessible data, including magnetic disk drives, optical disk drives, magnetic tape devices, and solid state memory devices. Furthermore, it should be appreciated that the data storage devices 224 and/or 228 may comprise large scale data storage systems, such as RAID systems. In addition, it should be appreciated that the data storage devices 224 and/or 228 may be distributed, rather than occupying one location. Furthermore, the external data storage devices 228 may be part of computers, such as general purpose or server computers, in communication with the controller 116. The information related to biological substrates 106 may be stored in the form of records comprising a database.

Figure 3:
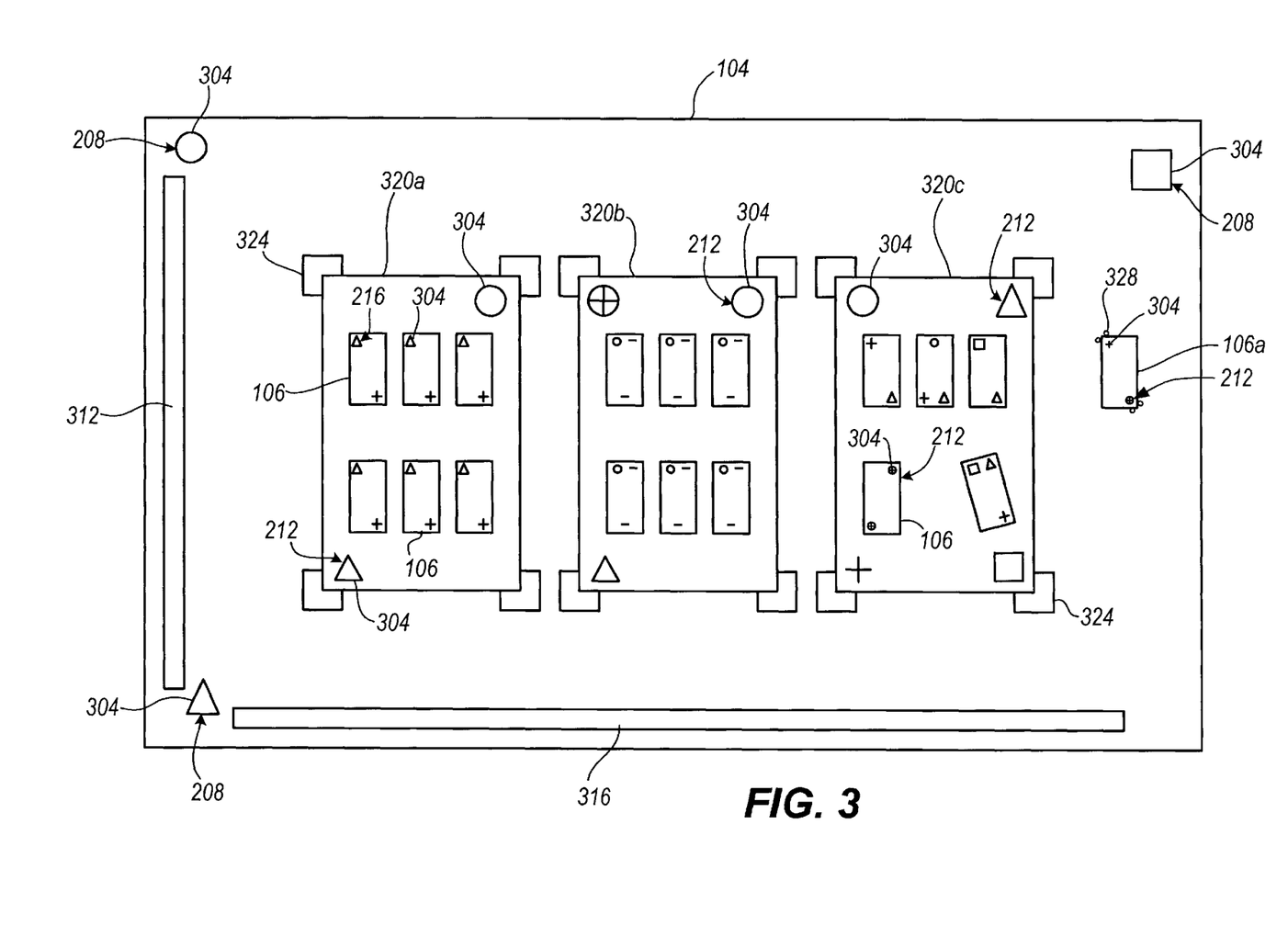
FIG. 3 is a plan view of a biological substrate platform in accordance with an embodiment of the present invention.

With reference now to FIG. 3, a biological substrate platform 104 in accordance with an embodiment of the present invention is illustrated in plan view. The biological substrate platform 104 illustrated in FIG. 3 includes a first fiducial level system 208 comprised of a plurality of fiducial marks 304. Accordingly, the position of the access device 108 with respect to the biological substrate platform 104 can be determined by signals provided to the controller 116 by an optical position sensor 144 making reference to the first fiducial level system 208. Alternatively or in addition, the position of the access device 108 relative to the biological substrate platform 104 may be determined by reference to signals derived from encoder strips and corresponding encoder sensors provided in connection with the various members 120–128 included in the carriage assembly 112. In accordance with still another embodiment of the present invention, the biological substrate platform 104 may include encoder strips 312 and 316 for providing information related to the relative position of the biological substrate platform 104 to the access device 108. For instance, the encoder strips 312, 316 are particularly useful in connection with embodiments of the system 100 having a movable biological substrate platform 104. Regardless of whether the biological substrate platform 104 or the access device 108 or both are movable, the fiducial marks 304 may be utilized to provide relative position information in connection with the optical sensor 144.

Also shown in FIG. 3 are a plurality of trays 320 that are held in position with respect to the surface of the biological substrate platform 104 by guide members 324. The trays 320 each have a number of associated biological substrates 106. According to an embodiment of the present invention, the biological substrates 106 associated with a particular tray 320 are positioned within recesses provided by the tray 320. Alternatively or in addition, a biological substrate 106 may be fixed to a tray 320 using mechanical or chemical means. Also shown in FIG. 3 is a biological substrate 106a interconnected directly to the biological substrate platform 104 by pins 328. It should be appreciated that the present invention does not require that both trays 320 and individual substrates 106 be capable of direct attachment to the biological substrate platform 104. Furthermore, it should be appreciated that guide members 324 and pins 328 may be used with either trays 320 or individual biological substrates 106, and that additional or alternative arrangements may be provided for interconnecting one or more trays 320 or biological substrates 106 to a biological substrate platform 104. For example, appropriately sized recesses may be formed in the biological substrate platform 104 that are each capable of receiving a tray 320, and/or recesses may be found in the biological substrate platform 104 that are each capable of receiving a biological substrate 106.

As illustrated in FIG. 3, the trays 320 may each include a second fiducial level system 212 comprising fiducial marks 304 that encompasses the entire working area of the respective tray 320. A second fiducial level system 212 is also illustrated in FIG. 3 that encompasses the entire working area of the biological substrate 106 interconnected directly to the biological substrate platform 104. Accordingly, in the example of FIG. 3, four separate second fiducial level systems 212 are illustrated. As can be appreciated, each of the second fiducial level systems 212 of FIG. 3 are in a sibling relationship with one another, and are located within an area encompassed by the first fiducial level system 208.

The individual biological substrates 106 associated with the trays 320 may also include fiducial marks 304. The fiducial marks 304 included on biological substrates 106 associated with a tray 320 comprise third fiducial level systems 216. The third fiducial level systems 216 are in a sibling relationship with one another. As can be appreciated, the third fiducial level systems 216 illustrated in FIG. 3 comprise non-overlapping sub-areas of the relevant second fiducial level system 212. As can further be appreciated, one or more third fiducial level systems 216 may encompass areas within a single second fiducial level system 212.

Figure 4:
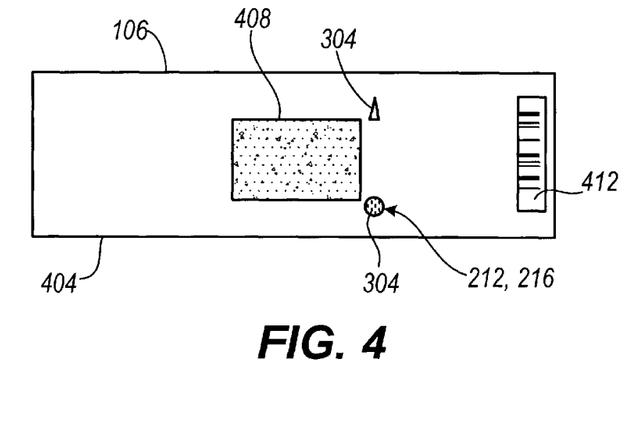
FIG. 4 is a plan view of a biological substrate in accordance with an embodiment of the present invention.

With reference now to FIG. 4, a biological substrate 106 in accordance with an embodiment of the present invention is illustrated. In general, the biological substrate 106 comprises a substrate 404 that provides support for a deposited material 408. The deposited material 408 may include any biological material under observation or in connection with which an operation is to be performed. For example, the deposited material 408 may include a tissue culture. The deposited material may be smeared on the substrate 404, or deposited in a well formed on the surface of the substrate 404.

Fiducial marks 304 are positioned adjacent the deposited material 408. In general, the fiducial marks 304 illustrated in FIG. 4 comprise a second fiducial level system 212 where a first or global level fiducial system 208 is associated with the biological substrate platform 104, and where the biological substrate 106 is positioned directly on the biological substrate platform 104, or is interconnected to the biological substrate platform 104 through a tray 320 that does not include any fiducial level system. The fiducial marks 304 in FIG. 4 also comprise a second fiducial level system 212 where the biological substrate 106 is interconnected to a biological substrate platform 104 that does not include a fiducial level system and is positioned within a tray 320 that includes a first fiducial level system 208. The fiducial marks 304 or the biological substrate 106 comprise a third fiducial level system 216 where, for example, the biological substrate 106 is positioned within a tray 320, the tray 320 has a second fiducial level system 212, and the biological substrate platform 104 has a first fiducial level system 208 associated therewith.

The biological substrate 106 may additionally include an identifier 412. The identifier 412 serves to uniquely identify the biological substrate 106 so that various information related to the biological substrate 106 that is stored separately from the biological substrate 106, such as in a database maintained in data storage 224, 228 associated with the controller 116, may be conveniently accessed or maintained. Information that may be usefully associated with a biological substrate 106, such as the biological substrate 106 illustrated in FIG. 4, may include information regarding the location of specific cells relative to the fiducial level system 212. Other information that may be usefully associated with a biological substrate 106 includes information identifying the deposited material 408, the date and time of deposition, the dates and results of any previous operations performed in connection with the substrate 106, and information regarding any bioactive components or surface preparations made with respect to the biological substrate 106. In the embodiment illustrated in FIG. 4, the identifier 412 is depicted as a bar code. A bar code is desirable because it is easily machine readable. Other suitable identifiers 412 include other optically perceivable indicia, such as alphanumeric codes, and machine readable indicia, such as magnetically or electronically encoded identifiers. As can be appreciated, an identifier 412 may comprise both machine readable and human readable components.

Figure 5:
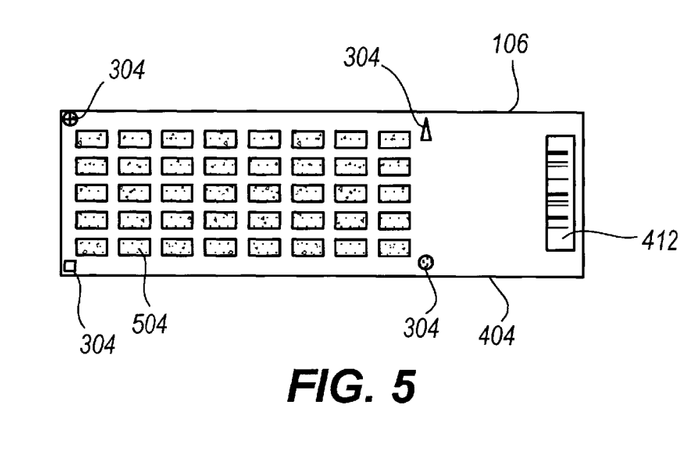
FIG. 5 is a plan view of a biological substrate in accordance with another embodiment of the present invention.

With reference now to FIG. 5, a biological substrate 106 in accordance with another embodiment of the present invention is illustrated. The biological substrate 106 illustrated in FIG. 5 includes a substrate 404 on which a plurality of discrete samples of a material 504 have been deposited. In particular, the samples of deposited material 504 are arranged in discrete rows and columns. Also shown in FIG. 5 is an identifier 412. As in the other embodiments of biological substrates 106 described herein, the identifier 412 associated with the biological substrate 106 generally serves to uniquely identify the biological substrate 106 so that various information related to the biological substrate 106 can be stored separately from the biological substrate 106. For example, the identifier 412 may relate the biological substrate 106 to information concerning the location and constitution of each of the samples 504 of deposited material on the substrate 404. In addition, the substrate 106 of FIG. 5 includes fiducial marks 304. The fiducial marks 304 of the biological substrate 106 in FIG. 5 comprise a third fiducial level system 216 where, for example, the biological substrate 106 is positioned within a tray 320, and the tray 320 has a second fiducial level system 212 associated therewith, and the platform has a first fiducial level system 208 associated therewith. Alternatively the fiducial marks 304 may comprise a second fiducial level system.

Figure 6:
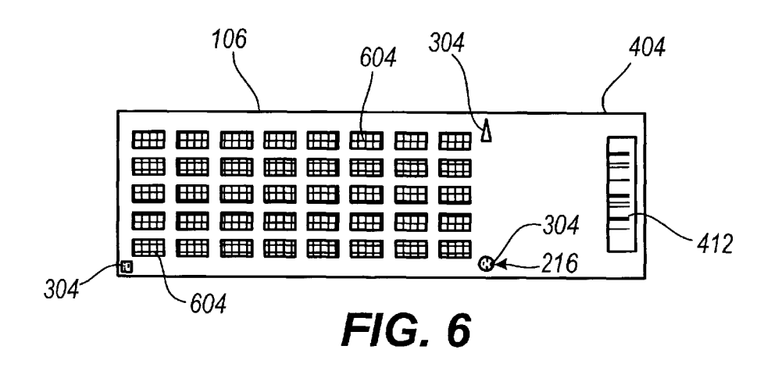
FIG. 6 is a plan view of a biological substrate in accordance with still another embodiment of the present invention.

With reference now to FIG. 6, a biological substrate 106, in accordance with yet another embodiment of the present invention, is illustrated. In general, the biological substrate 106 of FIG. 6 includes a substrate 404 on which a plurality of sub-regions 604 are established or defined. As shown in FIG. 6, the sub-regions 604 may be arranged in rows and columns. The biological substrate 106 also includes a plurality of fiducial marks 304. The fiducial marks 304 may comprise a first 208, a second 212 or a third fiducial level system 216. The biological substrate 106 may additionally include an identifier 412.

Figure 7:
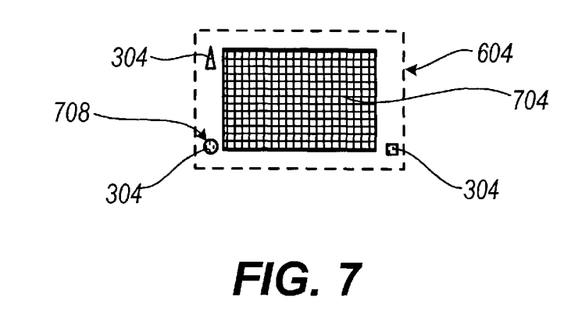
FIG. 7 is a detail of a subregion of the biological substrate illustrated in FIG. 6.

With reference now to FIG. 7, a sub-region 604 of a biological substrate 106, such as the biological substrate 106 illustrated in FIG. 6, is illustrated. The sub-region 604 may include a plurality of deposited material samples 704. As illustrated in FIG. 7, the material samples 704 may be arranged in rows and columns to form a grid. The intersection of the rows and columns form nodes that may correspond to the location of features, for example where the sub-region 604 comprises a microarray. Additionally, the sub-region 604 may comprise an array of wells formed in the substrate 404 for receiving deposited material 704. In accordance with another embodiment of the present invention, the samples of deposited material 704 may be placed at specific bioactive locations. In addition, the sub-region 604 includes a plurality of fiducial marks 304. The fiducial marks 304 comprise an additional fiducial level system 708. For example, the additional fiducial level system 708 comprises a fourth fiducial level system 708 where the biological substrate 106 includes a third fiducial level system 216 of fiducial marks 304, the biological substrate 106 is positioned within a tray that has a second fiducial level system 212, and the platform to which the tray 320 is interconnected has a first fiducial level system 208 associated therewith. The fiducial marks 304 associated with the sub-region 604 may alternatively comprise a third fiducial level system 216 where the biological substrate 106 is, for example, positioned directly on the biological substrate platform 104, and the biological substrate 106 has a second fiducial level system 212, and the biological substrate platform 104 has a first fiducial level system 208 associated therewith. Of course, the fiducial marks 304 may additionally comprise a second fiducial level system 208 if there is only one fiducial level system having an area of coverage that includes the sub-region 604. In general, each sub-region 604 associated with the biological substrate 106 may have associated therewith a plurality of fiducial marks 304.

In general, the method by which fiducial marks 304 are formed on a biological substrate platform 104, tray 320, or biological substrate 106 depends on the position sensor 144 of the system 100, and on the substrate 404 material. For example, where the position sensor 144 uses optical (e.g., machine vision) techniques for determining a position of the access device 108 relative to an area of interest (e.g., a sub-region 604 of a biological substrate 106), the fiducial marks 304 should be capable of being distinguished optically from surrounding areas of the associated element (e.g., the biological substrate platform 104, the tray 320, or the biological substrate 106). Thus, fiducial marks 304 for use in connection with an optical position sensor 144 may be formed by etching or engraving a fiducial mark 304 on a surface of the element. For example, a fiducial mark may be formed on a substrate 404 of a biological substrate 106 by altering the surface roughness of an area of a substrate 404 of a biological substrate 106 within a perimeter having the desired outline. As a further example of a suitable method of producing a fiducial mark 304 for use in connection with an optical position sensor 144, the fiducial marks 304 may be printed on the surface of the associated element. For example, ink may be deposited on a tray 320 in a desired pattern to form a fiducial mark 304. As a further example, a fluorescent dye may be deposited on a substrate 404 in a desired pattern to form a fiducial mark 304. Where a position sensor 144 utilizes a magnetic sensing technology, the fiducial marks 304 may be formed by, for example, depositing a magnetic material in a predetermined shape on an associated element. In accordance with an embodiment of the present invention, fiducial marks 304 are formed on an associated element by adhering a label, on which the desired fiducial marks 304 have been or may be printed, on the surface of the associated element.

Figure 8:
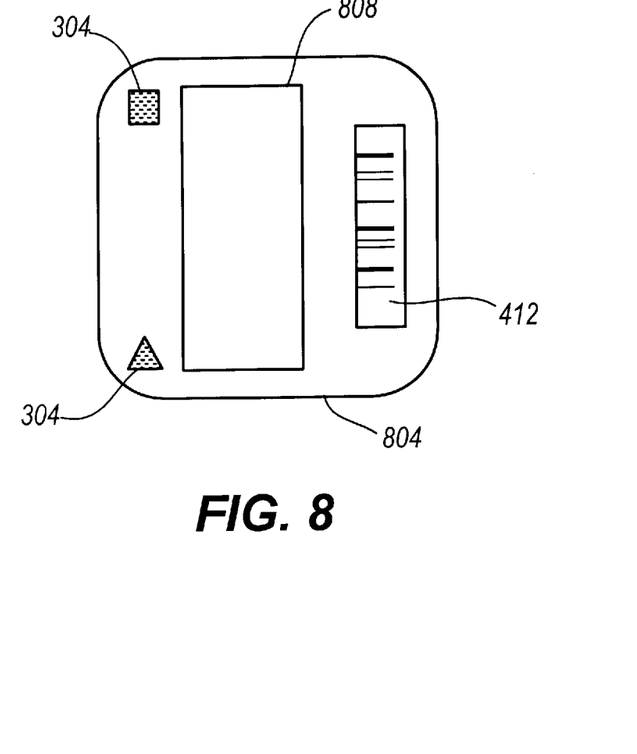
FIG. 8 is a plan view of a label containing fiducial marks and an identifier in accordance with an embodiment of the present invention.

With reference now to FIG. 8, a preprinted label 804 in accordance with an embodiment of the present invention is illustrated. The preprinted label 804 includes a plurality of fiducial marks 304. In addition, the preprinted label 804 includes a preprinted identifier 412. Accordingly, using a preprinted label 804, fiducial marks 304 and an identifier 412 may be associated with a biological substrate 106 simply by adhering the preprinted label 804 to the biological substrate 106. An aperture 808 may be formed in the label 804 to allow biological materials to be deposited directly on the substrate 404 of the biological substrate 106. Alternatively, where the label 804 is placed on a biological substrate 106 following the deposition of biological material on that substrate 404, the aperture 808 allows the label 804 to be positioned without disrupting the deposited biological material.

Figure 9:
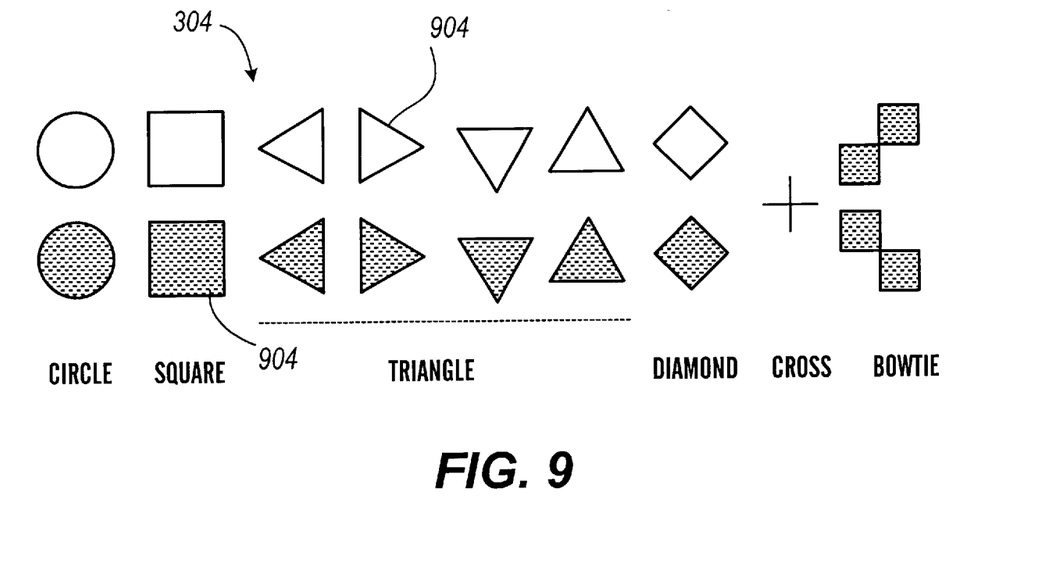
FIG. 9 contains illustrations of fiducial marks suitable for use in connection with a system for accessing a site on a biological substrate in accordance with an embodiment of the present invention.

With reference now to FIG. 9, examples of fiducial marks 304 suitable for use in connection with embodiments of the present invention are illustrated. As shown in FIG. 9, fiducial marks 304 may comprise distinct geometrical elements, such as circles, squares, triangles, diamonds, crosses and bow tie formations. Furthermore, the geometrical elements may have various orientations. In addition, the geometrical elements comprising fiducial marks may comprise outlines of the geometrical elements, or may comprise solid representations of those elements. Furthermore, it should be appreciated that a single fiducial mark 304 may comprise a combination of various elements 904. For example, a fiducial mark 304 may comprise a cross centered within the outline of a circle.

Machine vision techniques have been utilized in connection with fiducial marks to ensure the accurate assembly of electronic componentry. For example, machine vision techniques in combination with fiducial marks are used to align printed circuit boards (PCBs) and associated componentry in connection with repetitive manufacturing operations. In PCB manufacturing, individual boards are etched identically in panels of several boards. The individual boards may not be cut from the panel precisely. Accordingly, the position of the PCB pattern from the edges of the board may vary. By etching fiducial marks at the same time as the PCB pattern, the fiducial marks have the same relative position with respect to the elements of the PCB pattern, even though the position of the PCB pattern with respect to the edge of the board may vary from board to board. Machine vision has also been utilized in quality control applications.

However, machine vision technology has not been utilized in connection with the manipulation of biological materials. In addition, such techniques have not been attempted in connection with areas of interest that vary between particular instances of an item. For example, such techniques have not been applied in connection with slides containing tissue samples in which cells of interest may be at any location on the slide. Furthermore, machine vision has not been applied in applications in which an area of interest or a first slide may be located in a completely different portion of an area of interest on a second slide. In addition, machine vision has not been applied to align an access device in connection with a substrate having unique parameters. The use of multiple fiducial level systems is also unique to the present invention.

For example, in connection with microarrays, the placement of the pattern relative to the edges of a biological substrate 106 may vary. In addition, the array features may not necessarily align with an ideal array. This is because the deposition tools used to form the array are not highly precise, and accordingly the actual positions at which material is deposited will typically vary from substrate to substrate. The present invention allows for features to be precisely located. This capability is provided even though, unlike the case with printed circuit board manufacturing, the relative position of array features varies. In particular, in accordance with the present invention, fiducial marks 304 in connection with a global fiducial level system 208 may be utilized to locate the pattern on the substrate 106 generally. Fiducial marks 304 provided as part of a local fiducial level system 212, 216 may then be referred to identify the placement of features within the array.

In the present invention, global fiducial marks 304 are used to locate the position of features within a relatively large area. Specifically, with respect to the present invention, global fiducial marks 304 comprise a first fiducial level system 208, and are used for relatively coarse positioning operations. For example, global fiducial marks 304 may be used to align an array pattern grid relative to the edges of a substrate 404. Local fiducial marks 304 located within the area encompassed by the global fiducial marks are used for fine positioning operations. For example, local fiducial marks 304 associated with a local fiducial level system 212 or 216 may be utilized to locate or align particular features within an array of features. Preferably, three fiducial marks are utilized as part of a fiducial level system 208, 212 or 216. Typically, a first of the fiducial marks 304 is located at a point corresponding to the zero, zero datum point of the fiducial level system. The second and third fiducial marks are then located in the positive X and Y directions. Although the use of three fiducial marks 304 as part of a fiducial level system 208, 212 or 216 is generally preferred, a minimum of two fiducial marks 304 are needed for correction of translational offsets (e.g., the X and Y positions) and rotational offsets (theta position). When two fiducial marks 304 are used, they should be located diagonally opposed from one another, and as far apart from one another as possible. Fiducial level systems may also use a single fiducial mark, however such systems are typically capable of providing translational (e.g., X and Y) information only. If correction of non-linear distortions, such as scaling, stretch and twist, of a substrate are desired, at least three fiducial marks 304 are generally required. Preferably, the at least three fiducial marks 304 should be located in a triangular arrangement, with the marks as far apart from one another as possible. In a typical fiducial level system 208, 212 or 216, the fiducial marks 304 are of similar size and have a diameter of about 1.0 mm.

Figure 10:
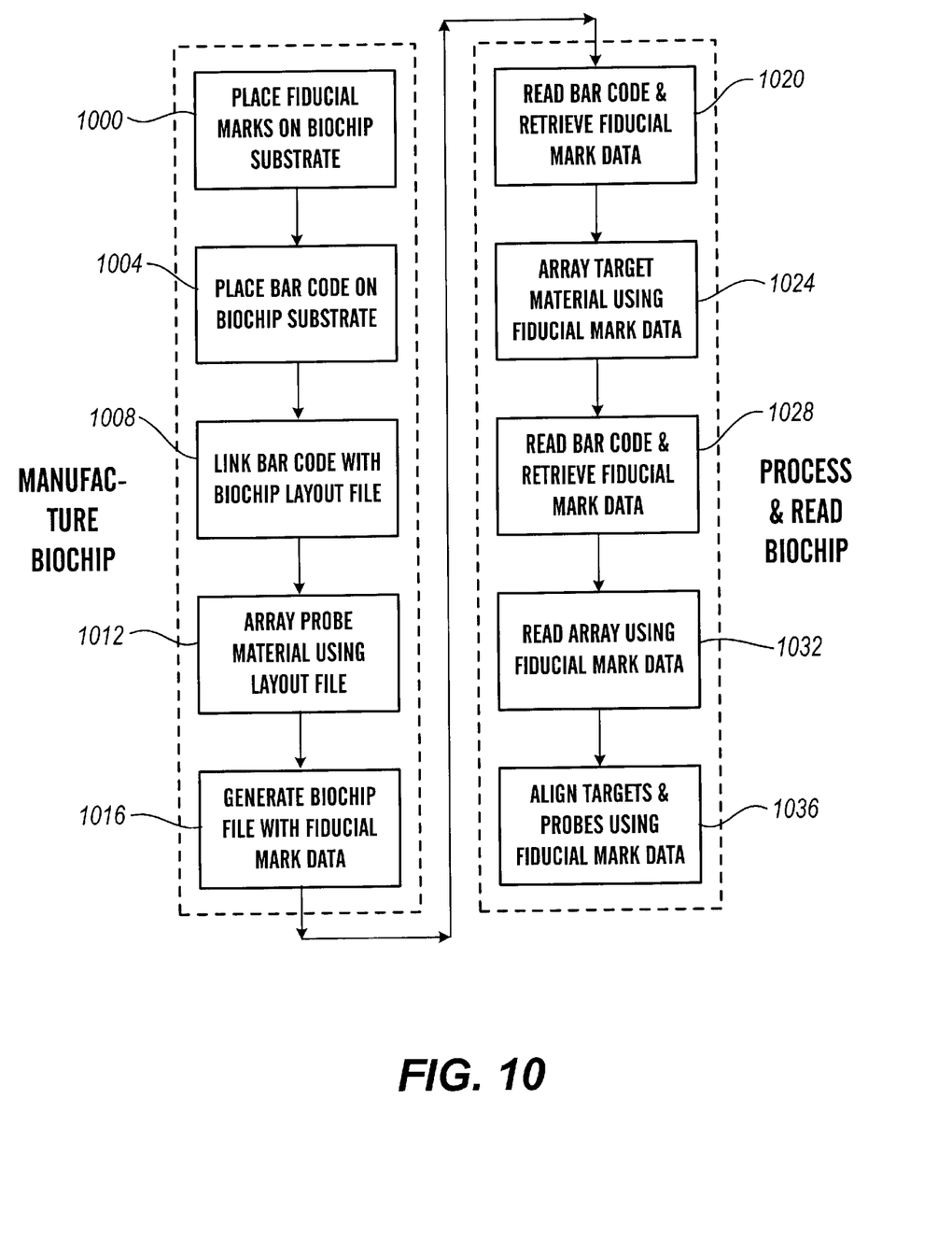
FIG. 10 is a flow chart illustrating biochip processing in accordance with an embodiment of the present invention.

With reference now to FIG. 10, a flow chart illustrating the use of a system 100 in accordance with an embodiment of the present invention is shown. In particular, FIG. 10 illustrates the use of a system 100 in connection with the manufacture and utilization of biochips. Initially, at step 1000, fiducial marks 304 are placed on the substrate 404 of the biological substrate 106, here a biochip. The fiducial marks 304 placed on the biological substrate 106 at step 1000 may comprise one or more fiducial level systems 208, 212 and/or 216. At step 1004, a bar code or other identifier 412 is positioned on the biological substrate 106. As noted above in connection with FIG. 8, the placement of fiducial marks 304 (step 1000) and the placement of an identifier 412 (step 1004) may be accomplished in a single step by placing a single preprinted label 804 on the biological substrate 106. A biochip layout file is next linked to the identifier 412 (step 1008). The layout file instructs the device 100 where to place or deposit probes on the substrate 404 relative to the fiducial marks 304. Alternatively, the probes are formed on the substrate 404, and a machine version device, such as the system 100 having a position sensor 144 is used to locate the probes sites relative to the fiducial marks 304. Accordingly, the layout file may contain information regarding the position of significant features on the biochip 106, such as sites that are biologically active, relative to the fiducial marks 304 formed on the substrate 404.

Biological material comprising the probes may then be arrayed on the biological substrate 106 at locations recorded in the layout file (step 1012). As can be appreciated, probes may, in addition to biologically active sites, comprise areas of the device having particular features, such as electrodes. Where the probes are features such as electrodes, those features may be formed on the substrate 404 in separate steps, such as during the manufacturing of the substrate 404. At step 1016, a file related to the biological substrate 106 is generated that includes data concerning the actual positions of the probes relative to fiducial marks 304 associated with the biochip 106.

Following the steps required to manufacture the biochip, the biochip 106 may be processed and read. In particular, by recording the position of the probes relative to the fiducial marks 106 provided in connection with a biological substrate 106 (such as a biochip 106), the probes can later be located with great precision. This allows target material to be accurately deposited on a probe. Furthermore, a result can be accurately assigned for each resulting probe and target pair, because the pairs can be located accurately and repeatedly.

Accordingly, at step 1020, the identifier 412, such as a bar code, associated with the biochip 106, may be read, and the biochip file containing the position of sites or features, such as probes, on the biochip 106 relative to the fiducial marks 304 is retrieved (step 1020). Where the biological substrate 106 contains more than one level of fiducial marks 304, the biochip file may contain data concerning the relative position of a fiducial level system covering a greater area (e.g., a second fiducial level system 212) with respect to a fiducial level system covering a subset of the area encompassed by that fiducial level system (e.g., a third fiducial level system 216). Furthermore, the biochip file may contain information regarding a global or first fiducial level system 208 that, for example, comprises fiducial marks 304 formed on the biological substrate platform 104 relative to a local fiducial level system 212 comprising fiducial marks 304 formed on the substrate of the biochip 106 when the biochip 106 is interconnected to the biological substrate platform 104. The biochip file may additionally include data concerning the location of particular sites or features on the biochip 106 relative to the most localized fiducial level system (e.g., the third fiducial level system 216), or to any other fiducial level system, whether at different positions in a hierarchy, or in a sibling relationship. Accordingly, the data associated with the biochip file may provide multiple data sets, allowing for the use of a variety of fiducial marks 304 as reference points in locating specific sites or features on the biological substrate 106. In addition, and particularly where a hierarchy of fiducial level systems is utilized, the data allows reference to be made initially to a relatively global fiducial level system (e.g., a second fiducial level system 212) for coarse positioning, which can be accomplished relatively quickly. In addition, the data file may contain information regarding the location of a probe site with respect to a relatively local fiducial level system (e.g., a third fiducial level system 216). Accordingly, relatively fine positioning may be accomplished by reference to a localized fiducial level system. Furthermore, the data contained in the biochip file may permit the use of alternate fiducial marks 304 or fiducial level systems 208–216 where, for example, the access device 108 is positioned in close proximity to a particular fiducial mark 304, or where a fiducial mark 304 that would normally be preferred for use in connection with a positioning operation (e.g., a fiducial mark 304 located in close proximity to a probe site) is obscured and unusable.

At step 1024, target material is arrayed using the fiducial mark data contained in the biochip file. The target material may be biologically active material. The data contained in the biochip file allows the target material to be deposited on the probes with a high degree of precision. In particular, the positioning accuracy provided by the use of fiducial marks 304, together with the position data stored in the biochip file, permits very high levels of positioning accuracy to be obtained, even while reducing the amount of time required to deposit the target material.

After the target material has been deposited on the active probe sites, reactions may be allowed to occur at the probe locations. For example, biological activity as a result of depositing target material on a biologically active target site may be allowed to occur over a period of time. Reactions between probes and deposited material that may be studied include DNA hybridization or antibody-antigen binding. As an example of a biological substrate 106 having physical features formed thereon that comprise probe sites, target material may be deposited on pairs of electrodes formed on the substrate 404, and an electrical potential 388 introduced between the pair of electrodes. The use of a layout file that contains information regarding the position of probe sites relative to the fiducial marks 304 included on a biological substrate 106 allows for target material to be precisely positioned on the probe sites, even when a first system or device 100 is used to deposit or form the probe locations, or to record the position of the probe locations, and a second system or device 100 is used to deposit the target material. That is, the use of a biochip file associated with a particular biological substrate 106 by an identifier 412 that records the position of features of the biological substrate 106 relative to fiducial marks allows those features to be reliably and repeatably accessed, even using different systems 100.

After the targets and corresponding probes react, the results of the reaction may be read using an appropriate access device 108. For example, an imaging device may be used. The access device 108 is positioned using the positioning data stored in the biochip file. Examples of results readouts include measurements of intensity, concentration, time sequence events, and spectral information. As part of reading the results of a reaction, fluorescence, absorption, radioactive decay, chemiluminescence, and other attributes of target sites may be detected. As with the deposition of the target material, the step of reading the array 1032 is facilitated by the precise location data that is available from the use of fiducial marks 304 in combination with the data contained in the biochip file. The material comprising the targets may vary from target to target. Therefore, at step 1036, information related to the target material is aligned with the probes, so that accurate information regarding the composition of the target at each probe can be recorded.

Figure 11:
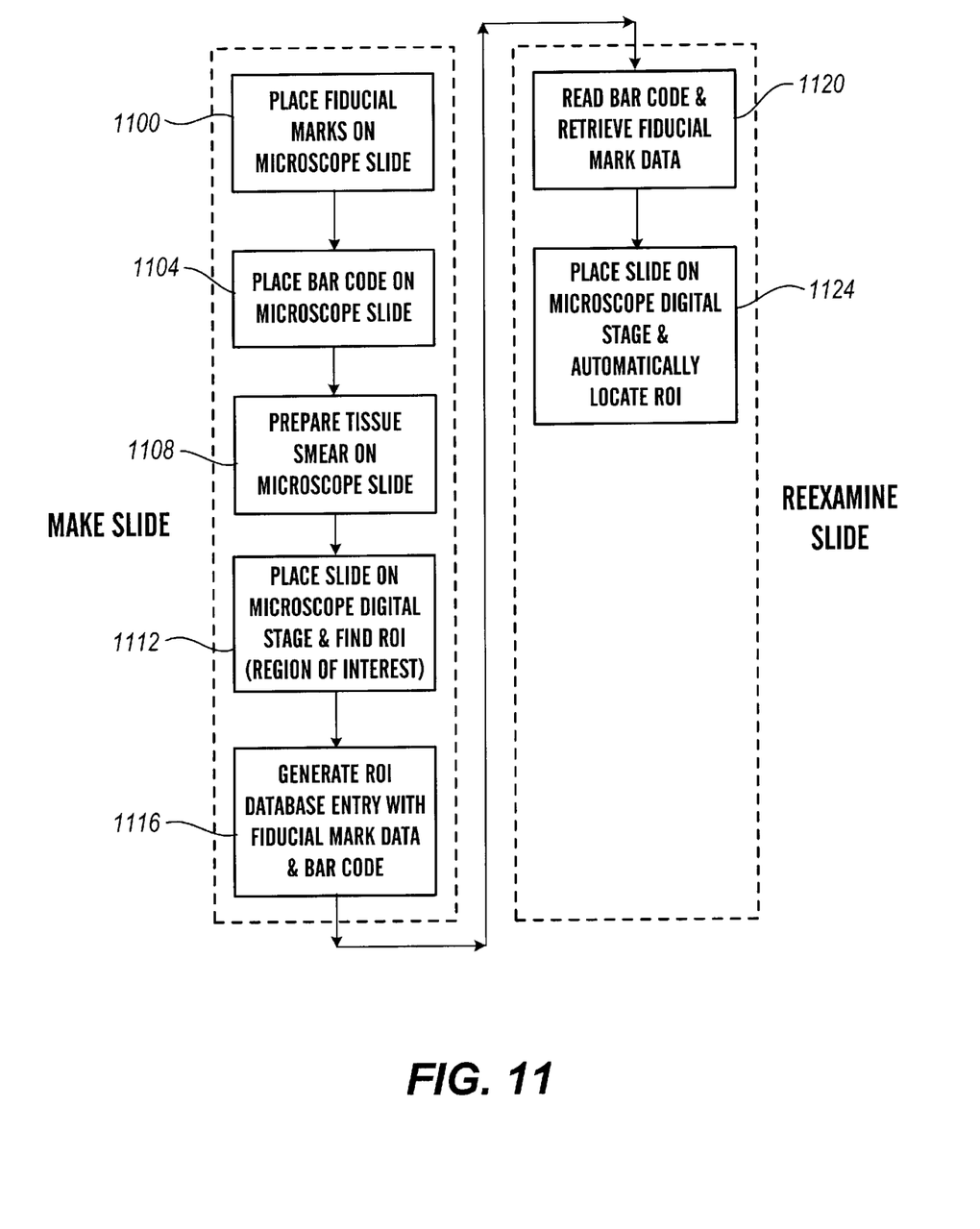
FIG. 11 is a flow chart illustrating slide processing in accordance with an embodiment of the present invention.

In FIG. 11, a flow chart depicting operations involving a biological substrate 106 comprising a slide containing a tissue sample is illustrated. Initially, at step 1100, fiducial marks are placed on the microscope slide (i.e. the substrate 404) (step 1100). At step 1104, an identifier 412, such as a barcode, is placed on the substrate 404. As noted above, the steps of placing fiducial marks 304 and an identifier 412 on a substrate 404 can be combined in a single step, for example when a preprinted adhesive label containing both fiducial marks 304 and an identifier 412 is used.

At step 1108, a tissue smear, a tissue section or cell culture material is prepared on the substrate 404 to complete the biological substrate or slide 106. In accordance with an embodiment of the present invention, the biological substrate or slide 106 can include a single biological sample or an array of one or more such samples. The biological substrate 106 is then placed on a microscope digital stage, and a region of interest or select features are identified by a technician (step 1112). Alternatively, a region or feature of interest can be identified automatically using an automated primary screening device. A file is then generated containing data concerning the location of the region of interest or the selected features with respect to the fiducial marks 304 (step 1116). In addition, the location data is stored in a file that is linked to the identifier 412 associated with the biological substrate 106. Steps 1100–1116 comprise those steps that are generally followed in creating a slide containing a tissue culture identifying a region of interest or feature set in accordance with an embodiment of the present invention.

At step 1120, the identifier 412 associated with the slide (i.e. biological substrate 106) is read, and the file containing the data concerning the relative position of feature(s) in the region or regions of interest to the fiducial marks 304 is retrieved. The slide may then be placed on the biological substrate platform 104 and the region of interest, or a selected region of interest, automatically located (step 1124). For example, one or more of the fiducial marks 304 associated with a first fiducial level system 208 are located by the position sensor 144. Data contained in the file associated with the biological substrate 106 is retrieved, for example from a database, and the position of one or more fiducial marks 304 associated with a second fiducial level system 212 is obtained. Data concerning the position of the feature in a region of interest relative to the second fiducial level system is also obtained. The actuators 204 may then be activated by the controller 116 to position the access device 108 (the microscope in the present example) such that the region of interest is within the field of view of the access device 108.

The biochip file contains information about the identification of the source material, location of the source material, the volume to be deposited, the order to be deposited, the feature location(s) (replicates within a substrate 106 and "n" substrates 106) where deposition will or has occurred relative to fiducial marks 304 (x offset, y offset, z offset, z rotation at a minimum). If the system is not orthogonal or the worksurface is not parallel with the ground or the scale changes then x rotations, y rotations, scale and possibly other information can be utilized. Additional information might include deposition parameters that are different for different types of materials (e.g., viscous or sticky). Deposition parameters might cover all aspects including picking, placing and washing. The file may include a header section that gives global instructions such as touch-off 10 times on a blank before spotting a real substrate. Information can be added to the file for later processing such as results of a visual inspection in which some features may be marked as unusable (skip mark). As a further example, the diameter of the spot is recorded as a measure of point-to-point variation.

Figure 12A:
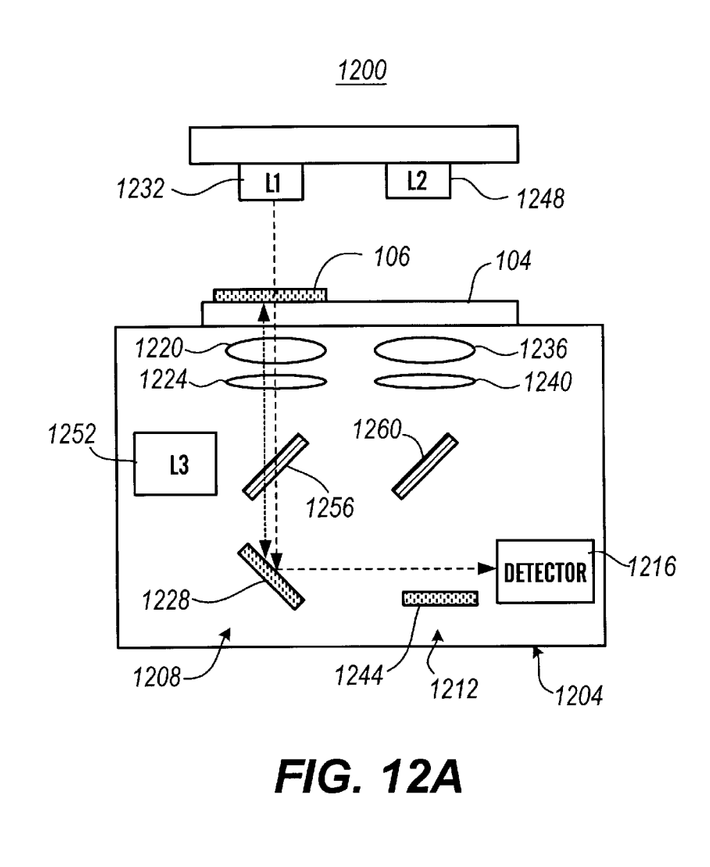
FIGS. 12A and 12B are schematic diagrams depicting an automated array imager in accordance with an embodiment of the present invention.
Figure 12B:
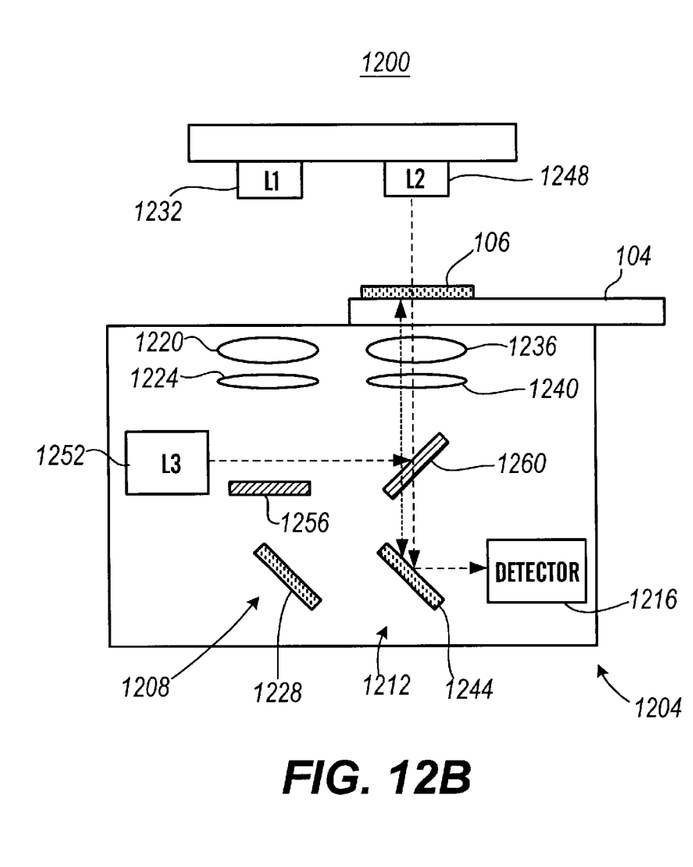

With reference now to FIGS. 12A and 12B, an automated array imager 1200 in accordance with an embodiment of the present invention is schematically depicted. In general, the automated array imager 1200 is modified with respect to the general system for accessing sites on a biological substrate 100 of the present invention, in that it incorporates an automatic positioning system 1204 for positioning the biological substrate platform 104 (and an attached biological substrate 106) relative to the access device 108. The automatic positioning system 1204 generally includes a global view or macro image unit 1208, a local view or microimage unit 1212, and a detector 1216. The macro image unit 1208 comprises a macro lens system 1220, an emission filter 1224, a mirror 1228, and a light source 1232. Similarly, the micro image unit 1212 comprises a micro lens system 1236, an emission filter 1240, a movable mirror 1244, and a light source 1248.

During a typical automated location operation, a biological substrate 106 is positioned on the biological substrate platform 104. The first light source 1232 is then operated to illuminate the fiducial marks 304 and the substrate 106. The macro lens system 1220 collects the light passing through both the fiducial marks 304 and the biological substrate 106 within a first field of view. The first field of view may encompass a relatively large area, such as the entire working area of a biological substrate 106. The light collected by the macro lens system 1220 is passed through the emission filter 1224, and any light that passes through the emission filter 1224 is directed to the detector 1216 by the mirror 1228. In accordance with an embodiment of the present invention, the emission filter 1224 passes light having wavelengths corresponding to wavelengths indicative of activity at sites on the biological substrate 106. For example, light associated with the fluorescence of sites at which biological activity is occurring may be allowed to pass through the emission filter element 1224. The position of the fluorescent material with respect to the biological substrate 106 can be determined by moving the macro image unit 1208 relative to the biological substrate 106. For example, such movement may be accomplished by moving the first light source 1232 relative to the biological substrate 106. In accordance with an embodiment of the present invention, the macro image unit 1208 may be synchronized to the access device 108, such that it moves with the access device 108.

Because the macro image unit 1208 operates over a fairly wide view angle, the macroimage unit 1208 is typically capable of identifying a region of potential interest on a biological substrate 106. The location of a region of interest can be determined based on the relative position of the region with respect to fiducial marks 304 provided as part of, e.g., the biological substrate platform 104, a tray 320, or a biological substrate 106. After identifying such a region, the micro image unit 1212 may be utilized to more precisely locate regions or sites at which activity of interest is occurring.

With reference now to FIG. 12B, the micro image unit 1212 is operated by projecting light from the second light source 1248 through the micro lens system 1236 and the micro emission filter 1240. As shown in FIG. 12B, the movable mirror 1244 is moved from a first position (see FIG. 12A) in which light from the macro image unit 1208 is not blocked by the movable mirror 1244, to a second position (see FIG. 12B). In the second or operative position, the movable mirror 1244 directs light passing through the micro lens system 1236 and the micro emission filter 1240 to the detector 1216. In general, the micro image unit 1208 has a narrower field of view than the macroimage unit 1208. This narrower field of view allows very small regions of the biological substrate 106 to be located with precision. In general, as with the macro image unit 1208, the micro image unit 1212 detects light of selected wavelengths emitted or passed by features on the biological substrate 106.

The region of interest (or hot spots) located using the macro image unit 1208 can be automatically located by the micro image unit 1212. In particular, the automatic positioning system 1204 can shift the relative position of the micro image unit 1212 and the biological substrate 106 such that the region of interest is within the field of view of the micro image unit 1212 when switching from use of the macro image unit 1208 to use of the micro image unit 1212. In particular, the micro image unit 1212 can locate fiducial marks 304 automatically. Then, using the recorded information regarding the position of a region of interest relative to the fiducial marks 304, a region of interest can be automatically located. The precise position of a feature in the region may be determined by moving the micro image unit 1212 relative to the biological substrate 106.

In addition or as an alternative to the first 1232 and second 1248 light sources, which are generally positioned above the biological substrate platform 104, a third light source 1252, located beneath the biological substrate platform 104, may be provided. The third light source 1252 may further provide wavelengths useful for fluorescence imaging. In connection with the third light source 1252, a movable dichroic mirror 1256 is provided. In particular, the movable dichroic mirror 1256 directs light from the third light source 1252 up through the macro lens system 1220 and the emission filter 1224 to the biological substrate 106 (see FIG. 12A). Light reflected off the biological substrate 104 then passes back through the lens system 1220, the filter 1224, and the movable dichroic mirror 1256, and is directed towards the detector by the mirror 1228.

When use of the third light source 1252 in connection with the micro image unit 1212 is desired, the movable dichroic mirror 1256 is moved so that it does not intercept the light from the third light source 1252. The light is then directed by a fixed dichroic mirror 1260 through the micro lens system 1236 and the micro emission filter 1240 to the biological substrate 106 (see FIG. 12B). Light reflected from the biological substrate 106 then passes back through the lens system 1236, the filter 1240, and the fixed dichroic mirror 1260, and is directed towards the detector 1216 by the movable mirror 1244.

The automated array imager 1200 facilitates the rapid and accurate location of features of interest. For example, the automated array imager system 1200 allows locations of interest to be identified automatically, such that a technician need not spend time performing that function. Instead, the technician may focus on assessing the activity at those sites that have been automatically located. Furthermore, it should be appreciated that the present invention facilitates the reaccessing of locations of interest even after a slide 106 has been removed from the device 1200 and later reinserted, or when different devices 1200 are used.

It should be appreciated that during automatic location operations, the position of regions or features of interest on a biological substrate 106 are marked relative to fiducial marks 304. For example, the location of a general region of interest may be recorded with respect to a global fiducial level system 208 encompassing the entire working surface of the biological substrate 106. Specific features or small regions of interest on the biological substrate 106 may be located with reference to local fiducial level systems 212, 216. The relative position of regions or features of interest may be recorded in files associated with the biological substrate 106. Accordingly, such regions may be located using the recorded coordinates during later operations performed in conjunction with a device 100 or 1200 in accordance with the present invention.

In an additional aspect of the present invention, the position of features relative to the origin or datum point associated with the device 100 is determined. In accordance with the present invention, the precise locations of biological substrates 106 or trays 320 is not required in order to accurately locate features of interest. Instead, the device 100 need only be taught the general location of such features. Such general location information may be utilized to locate fiducial marks 304 in the proximity of a desired region of interest. Data relative to the particular biological substrate 106 may then be accessed to precisely locate the region of interest. Accordingly, it should be appreciated that the present invention allows the use of similarly configured trays 320 and/or individual biological substrates 106 having features that can be located accurately, without requiring lengthy calibration of the device 100 each time the particular biological substrates 106 interconnected to the biological substrate platform 104 is changed. It should further be appreciated that the initial calibration of a device 100 in accordance with the present invention may be accomplished by scanning the entire surface for fiducial marks 304, and recording the relative positions of the fiducial marks 304.

Information may also be obtained from biological substrates 106 regarding the Z height of the substrate. Such information may be obtained, for example, during a step of forming features, such as a microarray, on a substrate 404. That information may then be recorded in a file associated with the biological substrate 106, that can be accessed during later access operations. Furthermore, it should be appreciated that Z height information may be recorded for individual features of a biological substrate 106. Such information may be particularly useful in connection with non-planar substrates 404, or in connection with features that are not coincidental with the surface of the substrate 404. Furthermore, a metric may be recorded and stored in a file concerning or characterizing any non-planar aspects of a substrate 404 that may affect the positioning of an access device 108 during access operations.

As can also be appreciated, a system 100 in accordance with the present invention may be utilized to access a source of material on a biological substrate 106. For example, samples placed in high density, multi-well biological substrates 106 may be picked up or aspirated using an access device 108. The access device 108 may be directed to a particular well using location information stored in a file that provides position information for the wells with respect to fiducial marks 304 on the biological substrate 106. Such functionality is particularly useful in connection with biological substrates 106 having a large number of wells, for example, biological substrates 106 having 1536 wells or more.

With respect to multi-well biological substrates 106, it should also be appreciated that the present invention can be applied to the deposition of biological material. For example, the present invention may be used to deposit biological material in selected wells of a high density (e.g., 1,536 wells per plate) multi-well biological substrate 106. As a further example, the present invention may be used in connection with depositing an array of biological material in the wells of a low density (e.g., 24 wells per plate) multi-well biological substrate 106.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described hereinabove are further intended to explain the best mode presently known of practicing the invention and to enable others skilled in the art to utilize the invention in such or in other embodiments and with various modifications required by their particular application or use of the invention. It is intended that the appended claims be construed to include the alternative embodiments to the extent permitted by the prior art.

What is claimed is:

1. A system for accessing selected areas of biological substrates, comprising:

a biological substrate;

a substrate tray operable to receive said biological substrate;

a platform operable to receive said substrate tray;

an access device;

a global fiducial level system located on at least one of said platform and said substrate tray, wherein said global fiducial level system is associated with a first area;

a local fiducial level system located on said biological substrate and associated with a second area;

a sensor, wherein said sensor senses said global fiducial level system to determine a position of said access device relative to said first area, and wherein said sensor senses said local fiducial level system to determine a position of said access device relative to said second area;

a substrate identifier; and a data storage device comprising at least a first data file associated with said substrate identifier, wherein information related to a position of a third area with respect to said local fiducial level system is stored in said at least a first data file.

2. The system of claim 1, wherein said biological substrate is interconnected to said tray, wherein said tray is interconnected to said platform, and wherein said global fiducial level system comprises a plurality of indicia formed on said tray.

3. The system of claim 1, wherein said global fiducial level system comprises a plurality of indicia formed on said platform.

4. The system of claim 1, wherein said local fiducial level system comprises a plurality of indicia formed on said substrate.

5. The system of claim 1, wherein said global fiducial level system and said local fiducial level system comprise a plurality of visible indicia.

6. The system of claim 5, wherein said sensor comprises an optical sensor.

7. The system of claim 1, wherein said second area is located within a perimeter defined by said first area.

8. The system of claim 1, wherein said platform is movable with respect to said access device.

9. The system of claim 8, further comprising:

an actuator for moving said platform with respect to said access device.

10. The system of claim 1, wherein said access device is movable wit respect to said platform.

11. The system of claim 10, further comprising:

an actuator for moving said access device with respect to said platform.

12. The system of claim 1, further comprising a plurality of substrates, wherein a unique substrate identifier is associated with each of said substrates.

13. The system of claim 1, further comprising a preprinted substrate label, wherein said substrate label comprises said substrate identifier and at least one of a global fiducial level system and a local fiducial level system.

14. The system of claim 1, wherein said access device comprises a microscope.

15. The system of claim 1, wherein said access device comprises a material deposition unit.

16. The system of claim 1, wherein said biological substrate comprises at least one of a microarray, a biochip, a biosensor, a multi-well assay plate, and a cytology slide.

* * * * *